United States Patent
Nakamura et al.

(10) Patent No.: US 6,387,933 B1
(45) Date of Patent: May 14, 2002

(54) INSECTICIDAL COMPOSITIONS AND INSECTICIDAL METHODS

(75) Inventors: Satoshi Nakamura, Osaka; Satoshi Sembo, Hyogo, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/890,122

(22) PCT Filed: Jan. 27, 1999

(86) PCT No.: PCT/JP99/00352

§ 371 Date: Jul. 27, 2001

§ 102(e) Date: Jul. 27, 2001

(87) PCT Pub. No.: WO00/44228

PCT Pub. Date: Aug. 3, 2000

(51) Int. Cl.⁷ .............................................. A01N 43/40
(52) U.S. Cl. ........................................ 514/345; 514/357
(58) Field of Search ................................. 514/345, 357

(56) References Cited

U.S. PATENT DOCUMENTS 5,994,331 A    11/1999   Erdelen et al. ............. 514/137

FOREIGN PATENT DOCUMENTS

WO         9637105        11/1996

*Primary Examiner*—Allen J. Robinson
(74) *Attorney, Agent, or Firm*—Birch, Stewart, Kolasch & Birch, LLP

(57) ABSTRACT

A pesticidal composition comprising (E)-$N^1$-[(6-chloro-3-pyridyl) methyl]-$N^2$-cyano-$N^1$-methylacetamidine and pyriproxyfen as active ingredients and a carrier, especially, the composition having the weight ratio of (E)-$N^1$-[(6-chloro-3-pyridyl)methyl]-$N^2$-cyano-$N^1$-methylacetamidine and pyriproxyfen in the composition is in the range of from 1:0.01 to 1:10. Further, a method for controlling pests applying an effective amount of (E)-$N^1$-[(6-chloro-3-pyridyl)methyl]-$N^2$-cyano-$N^1$-methylacetamidine and pyriproxyfen to plant or surrounding of plant. Furthermore, a method for controlling ectoparasites applying an effective amount of (E)-$N^1$-[(6-chloro-3-pyridyl)methyl]-$N^2$-cyano-$N^1$-methylacetamidine and pyriproxyfen to host animal.

8 Claims, No Drawings

INSECTICIDAL COMPOSITIONS AND INSECTICIDAL METHODS

This application is the national phase under 35 U.S.C. § 371 of PCT International Application No. PCT/JP99/00352 which has an International filing date of Jan. 27, 1999, which designated the United States of America and was not published in English.

TECHNICAL FIELD

The present invention relates to pesticidal compositions and pesticidal methods.

BACKGROUND ARTS

Pesticides for controlling various pests such as agricultural and forestry pests, ectoparasites of animals and insanitary pests have been developed, and organophosphorus compounds, carbamate compounds, pyrethroid compounds, insect growth regulating substances and so on have been utilized so far. In some cases of application, however, it cannot be said that they exhibit satisfactory effects.

The present invention provides pesticidal compositions and pesticidal methods which are very effective for controlling the pests in agricultural and forestry fields, and further effective for controlling ectoparasites of animals, insanitary pests and the other various pests.

DISCLOSURE OF THE INVENTION

The present invention solved the problems by a pesticidal composition comprising (E)-$N^1$-[(6-chloro-3-pyridyl)methyl]-$N^2$-cyano-$N^1$-methylacetamidine and 4-phenoxyphenyl 2-(2-pyridyloxy)propyl ether as active ingredients and a pesticidal method comprising utilizing (E)-$N^1$-[(6-chloro-3-pyridyl)methyl]-$N^2$-cyano-$N^1$-methylacetamidine and 4-phenoxyphenyl 2-(2-pyridyloxy)propyl ether together.

Namely, the present invention provides a pesticidal composition (hereinafter, referred to as the present pesticidal composition) comprising (E)-$N^1$-[(6-chloro-3-pyridyl)methyl]-$N^2$-cyano-$N^1$-methylacetamidine (hereinafter, referred to as acetamiprid) and 4-phenoxyphenyl 2-(2-pyridyloxy)propyl ether (hereinafter, referred to as pyriproxyfen) as active ingredients and a pesticidal method (hereinafter, referred to as the present pesticidal method) comprising utilizing acetamiprid and pyriproxyfen together.

Acetamiprid used in the present pesticidal composition and the present pesticidal method is a compound described in U.S. Pat. No. 5,304,566 specification and pyriproxyfen is a compound described in U.S. Pat. No. 4,751,225 specification. These compounds can be produced according to the descriptions in these specifications. Further, acetamiprid or pyriproxyfen on the market can be used.

The combination of acetamiprid and pyriproxyfen produces a synergistic effect that is clearly larger than a sum of the sole effect of each compound as shown in the test examples described later.

In the present pesticidal composition and the present pesticidal method, acetamiprid and pyriproxyfen are combined and utilized in a ratio that can produce a synergistic effect. It is usually 0.01 to 10 parts by weight of pyriproxyfen, preferably 0.05 to 5 parts by weight based on 1 part by weight of acetamiprid.

The present pesticidal composition and the present pesticidal method can be applied for controlling various pests such as agricultural and forestry pests, ectoparasites of animals and insanitary pests. Examples of the pest include Hemipteran pests such as Delphacidae (planthoppers) [e.g. *Laodelphax striatellus* (small brown planthopper), *Nilaparvata lugens* (brown planthopper) and *Sogatella furcifera* (white-backed rice planthopper)], Deltocephalidae (leafhoppers) [e.g. *Nephotettix cincticeps* and *Nephotettix virescens*], Aphididae (aphids) [e.g. *Aphis gossypii* (cotton aphids), *Myzus persicae* (green peach aphid), *Aphis citricola*, *Lipaphis pserudobrassicae* (turnip aphid), *Nippolachnus piri*, *Toxoptera aurantii* (black citrus apid) and *Toxoptera citricidus* (brown citrus apid)], stink bugs [e.g. *Nezara antennata* (green stink bug), *Cletus punctiger*, *Riptortus clavetus* (bean bug) and *Plautia stali* (oriental stink bug)], Aleyrodidae (whiteflies) [e.g. *Trialeurodes vaporariorum* (greenhouse whitefly), *Bemisia tabaci* (sweetpotato whitefly) and *Bemisia argentifolli* (silverleaf whitefly)], scales, Tingidae (lace bugs) and Psyllidae (suckers); Lepidopteran pests such as Pyralidae [e.g. *Chilo suppressalis* (rice stem borer), *Cnaphalocrocis medinalis* (rice leafroller), *Ostrinia nubilalis* (European cornborer), *Parapediasia teterrella* (bluegrass webworm), *Notarcha derogata* (cotton leafroller) and *Plodia interpunctella* (Indian meal moth)], Noctuidae [e.g. *Spodoptera litura* (tobacco cutworm), *Pseudaletia separata* (rice armyworm), *Mamestra brassicae* (cabbage armyworm), *Agrotis ipsilon* (black cutworm), Trichoplusia spp., Heliothis spp. and Helicoverpa spp.], Pieridae [e.g. *Pieris rapae*], Tortricidae [e.g. Adoxophyes spp., *Grapholita molesta* (oriental fruit moth) and *Cydia pomonella*], Carposinidae [e.g. *Carposina niponensis* (peach fruit moth)], Lyonetiidae [e.g. Lyonetia spp.], Lymantriidae [e.g. Lymantria spp. and Euproctis spp.], Yponameutidae [e.g. *Plutella xylostella*], Gelechiidae [e.g. *Pectinophora gossypiella* (pink bollworm)], Arctiidae (tiger moths) [e.g. *Hyphantria cunea* (fall webworm)] and Tineidae [e.g. *Tinea translucens* (casemaking clothes moth) and *Tineola bisselliella* (webbing clothes moth)]; Dipteran pests such as Culex spp. [e.g. *Culex pipiens pallens* and *Culex tritaeniorhynchus*], Aedes spp. [e.g. *Aedes albopictus*], Anopheles spp. [e.g. *Anopheles sinensis*], Chironomidae (midges), Ceratopogonidae (biting midges) [e.g. *Culicoides oxystoma*], Muscidae [e.g. *Musca domestica* (housefly), *Muscina stabulans* (false housefly), *Musca hervei* and *Musca bezzii*], Calliphoridae, Sarcophagidae, Fannia spp. (little house flies), Anthomyiidae [e.g. *Delia platura* (seedcorn maggot) and *Delia antiqua* (onion maggot)], Tephritidae (fruit flies), Drosophilidae (vinegar flies), Psychodidae (sand flies), Simuliidae (black flies) [e.g. *Simulium iwatens*], Tabanidae [e.g. *Tabanus chrysurus*], Stomoxyidae (stable flies) [e.g. *Haematobia irritans*] and Agromyzidae (leafminer flies); Coleopteran pests such as corn rootworms [e.g. *Diabrotica virgifera virgifera* (western corn rootworm) and *Diabrotica undecimpunctata howardi* (southern corn rootworm)], Scarabaeidae [e.g. *Anomala cuprea* and *Anomala rufocuprea*], Curculionidae (weevils) [e.g. *Sitophilus zeamais* (maize weevil), *Lissorhoptrus oryzophilus* (ricewater weevil), *Hypera pastica* (alfalfa weevil) and *Callosobruchuys chienensis* (adzuki bean weevil)], Tenebrionidae (darkling beetles) [e.g. *Tenebrio molitor* (yellow mealworm) and *Tribolium castaneum* (red flour beetle)], Chrysomelidae (leaf beetles) [e.g. *Aulacophora femoralis* (cucurbit leaf beetle), *Phyllotreta striolata* (striped flea beetle) and *Leptinotarsa decemlineata* (Colorado beetle)], Anobiidae, Epilachna spp. [e.g. *Epilachna vigintioctopunctata*], Lyctidae (powderpost beetles), Bostrychidae, Cerambycidae and *Paederus fuscipes*; Dictyopteran pests such as *Blattella germanica* (German cockroach), *Periplaneta fuliginosa* (smokybrown cockroach), *Periplaneta americana* (American cockroach), *Periplaneta brunnea* (brown cockroach) and *Blatta orientalis*; Thysanopteran pests such as *Thrips palmi, Thrips tabaci, Thrips hawaiiensis* (flower thrips), *Scirtothrips dorsalis* (yellow tea thrips), *Frankliniella intonsa* (flower thrips), *Frankiniella occidentalis* (western flower thrips) and *Ponticulothrips diospyrosi*; Hymenopteran pests such as Formicidae (ants), Vespidae (hornets), Bethylidae and Tenthredinidae (sawflies) [e.g. *Athalia japonica* (cabbage sawfly)]; Orthopteran pests such as Gryllotalpidae (mole crickets) and Acrididae (grasshoppers); Siphonapteran pests such as *Pulex irritans* (human flea), *Ctenocephalides felis* (cat flea) and *Ctenocephalides canis* (dog flea); Anopluran pests such as *Pediculus humanus corporis, Phthirus pubis* (crab louse), *Haematopinus eurysternus* (cattle louse) and *Damalinia ovis* (sheep louse); Isopteran pests such as *Reticulitermes speratus* and *Coptotermes formosanus*; Acarina such as Tetranychidae (spider mites) [e.g. *Tetranychus urticae* (two-spotted spider mite), *Tetranychus kanzawai* (Kanzawa spider mite), *Panonychus citri* (citrus red mite), *Panonychus ulmi* (European red mite) and *Oligonychus* spp.], Eriophyidae [e.g. *Aculops pelekassi* (pink citrus rust mite) and *Calacarus carinatus* (purple tea mite)], Tarsonemidae [e.g. *Polyphagotarsonemus latus*], Ixodidae [e.g. *Haemaphyxalis longicornis* and *Boophilus microplus*] and house dust mites [e.g. Acaridae, Cheyletidae and chicken mites]; and Nematoda such as *Pratylenchus coffeae* (coffee root-lesion nematode), *Pratylenchus fallax, Pratylenchus loosi, Pratylenchus vulnus* (walnut root-lesion nematode), *Heterodera glycines* (soybean cyst nematode), *Globodera rostochiensis* (potato cyst nematode), *Meloidogyne hapla* (northern root-knot nematode) and *Meloidogyne incognita* (southern root-knot nematode).

In the present pesticidal method, each of acetamiprid or its formulation and pyriproxyfen or its formulation can be used simultaneously, but it is convenient to use the present pesticidal composition in which acetamiprid and pyriproxyfen are mixed with each other in advance.

The present pesticidal composition comprises acetamiprid and pyriproxyfen as active ingredients and an inert carrier. The inert carrier can be solid carriers, liquid carriers and the like which are utilized for usual pesticidal formulations. The present pesticidal composition can optionally comprise formulation auxiliaries such as surfactant, dispersant, adhesive agent, stabilizer and propellant to be formulated to oil solution, emulsifiabe concentrates, wettable powders, flowables such as aqueous suspension and aqueous emulsion, lotion, spot-on formulation, pour-on formulation, shampoo, granules, dusts, tablet, injection formulation, aerosol, foaming aerosol, ULV formulation, poison bait, sheet formulation and resin formulations such as collar, medallion and ear-tag.

Examples of the solid carrier include fine powders and granules of clays such as kaolin clay, diatomaceous earth, bentonite and terra alba; synthetic hydrated silicon oxide; talc and the like; ceramics; the other inorganic minerals such as sericite, quartz, sulfur, activated carbon, calcium carbonate and hydrated silica; chemical fertilizers such as ammonium sulfate, ammonium phosphate, ammonium nitrate, urea and ammonium chloride. Examples of the liquid carriers include water; alcohols such as methanol and ethanol; ketones such as acetone and methyl ethyl ketone; aromatic hydrocarbons such as toluene; aliphatic hydrocarbons such as hexane, kerosene, paraffin and petroleum benzine; esters such as ethyl acetate and butyl acetate; ethers such as tetrahydrofuran and dioxane; halogenated hydrocarbons such as dichloroethane, trichloroethane and carbon tetrachloride. The present composition may be formulated by added a propellant such as propane gas, butane gas, chlorinated petroleum gas, freon gas, dimethyl ether and carbon dioxide thereto.

Examples of the surfactant include alkyl sulfate esters, alkylarylsulfonate salts, alkylaryl ethers and its polyoxyethylenated derivatives, polyethyleneglycol ethers, polyvalent alcohol esters and sugar alcohol derivatives.

Examples of the other auxiliaries such as adhesive agents and dispersants include casein; gelatin; saccharides such as starch, gum arabic, cellulose derivatives and alginic acid; lignin derivatives; bentonite; and synthetic water-soluble polymers such as polyvinyl alcohol, polyvinylpyrrolidone and polyacrylic acids. Further, stabilizers including PAP (isopropyl acid phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, fatty acids and fatty acid esters can be utilized as formulation auxiliaries.

The materials for resin formulation are exemplified by vinyl chloride polymers and polyurethane, to which a plasticizer, for example, phthalic acid esters such as dimethyl phthalate and dioctyl phthalate, adipic acid esters and stearic acid, may be optionally added. In preparing the resin formulations, the pesticidal ingredients are mixed with the material and kneaded with a usual device, and then molded by injection, extrusion, press and so on. The molded pesticidal composition can be subjected to a step such as further molding and cutting to be sheet, attractive string, garden pole, animal collar, medallion and ear-tag.

In the present pesticidal composition and the present pesticidal method, the other insecticide, nematocide, acaricide, repellent, fungicide, herbicide, plant growth regulator, synergist, fertilizer, soil improving agent or animal food may be used simultaneously.

Examples of the insecticide, nematocide and acaricide include pyrethroid compounds such as permethrin, cypermethrin, fenvarelate, esfenvarelate, fenpropathrin, biphenthrin, deltamethrin, fluvalinate, flucythrinate, allethrin, d-allethrin, prallethrin, cyphenothrin, phenothrin, resmethrin, tefluthrin, empenthrin, acrinathrin, cyhalothrin, cyfluthrin, etofenprox, halfenprox, silafluofen, tralomethrin, cycloprothrin, esbiothrin, transfluthrin, terallethrin and 1-ethynyl-2-fluoro-2-pentenyl 3-(2,2-dichlorovinyl)-2,2-dimethylcyclopropanecarboxylate; organophosphorus compounds such as cyanophos, fenthion, fenitrothion, parathion, methylparathion, pirimiphos-methyl, diazinon, isoxathion, pyridaphenthion, chlorpyrifos, chlorpyrifos-methyl, oxydeprofos, vamidothion, malathion, phenthoate, dimethoate, thiometon, disulfoton, phosalone, phosmet, methidathion, prothiofos, sulprofos, profenofos, azinphosmethyl, pyraclofos, calvinphos, salithion, tetrachlorvinphos, dichlorvos, monocrotophos, naled, dimethylvinphos, propaphos, acephate, metamidofos and ethion; carbamate compounds such as carbaryl, metolcarb, isoprocarb, fenobcarb, propoxur, XMC, ethiofencarb, bendiocarb, pyrimicarb, carbosulfan, carbofuran, benfuracarb, furathiocarb, methomyl, thiodicarb, oxamyl, alanycarb, fenothiocarb, metoxadiazone and fenothiocarb; formamidine derivatives such as N-methyl-bis(2,4-xylyliminomethyl)amine, N'-(4-chloro-2-methylphenyl)-N, N-dimethylformamidine; N-phenylpyrazole derivatives; N-tert-butyl-N'-(4-ethylbenzoyl)-3,5-dimethylbenzhydrazide; 4-bromo-2-(4-chlorophenyl)-1-ethoxymethyl-5-(trifluoromethyl)pyrrole-3-carbonitrile; nereistoxin derivatives such as cartap, bensultap and thiocyclam; chlorinated hydrocarbon compounds such as benzoepin, dicofol and tetradifon; formamidine derivatives such as amitraz and chlordimeform; phenylpyrazole derivatives such as ethiprole; tebufenozide; methoxyfenozide; halofenozide; chromafenozide; chlorfenapir; phenisobromolate; quinomethionate; propargit; fenbutatin oxide; hexythiazox; clofentezine; etoxazole; pyridaben; fenpyroximate; tebufenpyrad; pyrimidifen; polynactin complex; milbemectin; avermectin; ivermectin; and azadirachtin.

Examples of the repellent include carane-3,4-diol, N,N-diethyl-m-toluamide (Deet), limonene, linalol, citronellal, menthol, hinokitiol, geraniol and eucalyptol. Further, the present pesticidal composition can be used with aryldiazole compounds or 2-methoxycarbonyl-4-chlorotrifluoromethanesulfonanilide. Furthermore, the present pesticidal composition may comprise antioxidant such as butylhydroxyanisole, dibutylhydroxytoluene, tocopherol and γ-oryzanol; synergist such as bis(2, 3,3,3-tetrachloropropyl) ether, N-(2-ethylhexyl)bicyclo[2.2.1]hept-5-ene-2, 3-dicarboximide and α-[2-(2-butoxyethoxy)ethoxy]-4,5-methylenedioxy-2-propyltoluene; and stabilizer.

The present pesticidal method is an application of an effective amount of acetamiprid and pyriproxyfen to pest or a place where pests inhabit. Typical methods are explained as below.

In case of controlling agricultural or forestry pests by the present pesticidal method, the application rate of acetamiprid and pyriproxyfen is usually 1 g to 1000 g, preferably 10 g to 300 g per 1 hectare at the total amount of the ingredients. In the present pesticidal method, the concentration is usually 10 ppm to 1000 ppm at the total amount of the active ingredients, when the present pesticidal composition such as emulsifiable concentrates, wettable powders and flowables is diluted with water and applied. Granules and dusts of the present pesticidal composition are applied as they are.

In the present pesticidal method, acetamiprid and pyriproxyfen may be supplied to foliar application to plants those are crops to be protected from agricultural and forestry pests, or soil treatment to the surroundings of the plants for making the active ingredients absorbed from their roots. Soil treatment can also control agricultural and forestry pests those inhabit in soil. Further, the resin formulations formed to sheet or string can be applied by winding around the plants, setting or covering on the soil surface of the surroundings of the plants.

When the present pesticidal method is applied for controlling ectoparasites of animals, examples of the objective host animals include domestic animals such as cattle, sheep, goat, cock and hen; pets and experimental animals such as dog, cat, mouse, rat, hamster, squirrel, rabbit, ferret, duck and pigeon; and so on.

The application rate of acetamiprid and pyriproxyfen to these animals is generally 0.002 g to 0.2 g per 1 kg of the animal weight at the total amount of both compounds. When the formulated pesticidal composition is used, the content of acetamiprid and pyriproxyfen in the formulation is usually 0.001 to 40% by weight, preferably 0.01 to 20% by weight at the total amount of both compounds though it depends on formulation type and application method.

These formulations can give controlling effect by applying to ectoparasite of animals directly. Especially, parenteral or oral administration to host animals can control the ectoparasite effectively. Typical methods for controlling ectoparasites of animals are systemic methods such as oral administration, injection, implant and spot-on for controlling the pests via blood of the host animals and non-systemic methods such as pour-on, collar, medallion and tag.

EXAMPLES

The present pesticidal composition and the present pesticidal method will be explained in detail below. However, the present invention is not limited to these examples. In the following formulation examples, part means part by weight.

Formulation Example 1 Aerosol

One-tenth (0.1) part of acetamiprid and 0.01 part of pyriproxyfen are dissolved in ethanol to make the total 35 parts and put into an aerosol container. After attaching a valve with the aerosol container, 65 parts of LPG (propellant) are charged under pressure to give an aerosol.

Formulation Example 2 Emulsifiable Concentrate

Ten parts of acetamiprid, 5 parts of pyriproxyfen, 8 parts of polyoxyethylenealkyl aryl ether, 2 parts of sodium alkylarylsulfonate and 75 parts of xylene are mixed uniformly to give an emulsifiable concentrate.

Formulation Example 3 Wettable Powders

Ten parts of acetamiprid, 10 parts of pyriproxyfen, 3 parts of sodium alkylbenzenesulfonate, 3 parts of sodium ligninsulfonate and 74 parts of diatomaceous earth are mixed uniformly and pulverized by jet air mill to give wettable powders.

Test Example 1

Cabbage seedlings planted in 3 ounces plastic cup were placed in a net cage containing many living silverleaf whiteflies for 24 hours, so that many silverleaf whiteflies became parasitic on the cabbage seedlings. A designated amount of each of acetamiprid on the market (commercial name, Mospilan water-soluble powder: produced by Nippon Soda), pyriproxyfen on the market (commercial name, Lano emulsifiable concentrate: produced by Sumitomo Chemical) and a mixture of acetamiprid and pyriproxyfen on the market were diluted with water, and then sprayed over the cabbage seedlings with spray gun. The number of silverleaf whiteflies (i.e., the total number of adults and larvae) surviving on the cabbage seedlings was examined just before and after 8 days from the treatment. The test results are shown in table 1.

TABLE 1

| Compound | Concentration (ppm) | Number of surviving insects/pot | |
| --- | --- | --- | --- |
| | | before | after 8 days |
| acetamiprid | 50 | 114 | 69 |
| pyriproxyfen | 50 | 65 | 21 |
| acetamiprid + pyriproxyfen | 12.5 + 12.5 50 + 50 | 153 118 | 0 0 |
| No treatment | — | 96 | 88 |

Test Example 2

Cabbage seedlings planted in 3 ounces plastic cup were placed in a net cage containing many living silverleaf whiteflies for 24 hours, so that many silverleaf whiteflies became parasitic on the cabbage seedlings. A designated amount of each of acetamiprid on the market (commercial name, Mospilan water-soluble powder: produced by Nippon Soda), pyriproxyfen on the market (commercial name, Lano emulsifiable concentrate: produced by Sumitomo Chemical) and a mixture of acetamiprid and pyriproxyfen on the market were diluted with water, and then sprayed over the cabbage seedlings with spray gun. The number of silverleaf whiteflies (i.e., the total number of adults and larvae) surviving on the cabbage seedlings was examined just before and after 8 days from the treatment. The test results are shown in table 2.

TABLE 2

| Compound | Concentration (ppm) | Number of surviving insects/pot | |
|---|---|---|---|
| | | before | after 8 days |
| acetamiprid | 5 | 169 | 41 |
| | 10 | 173 | 16 |
| | 50 | 270 | 24 |
| pyriproxyfen | 5 | 140 | 41 |
| | 10 | 206 | 114 |
| | 50 | 391 | 69 |
| acetamiprid + pyriproxyfen | 50 + 5 | 223 | 0 |
| | 50 + 10 | 105 | 0 |
| | 10 + 50 | 128 | 0 |
| | 5 + 50 | 227 | 3 |
| No treatment | — | 171 | 144 |

Test Example 3

One-fifties gram (0.02 g) of acetamiprid and 0.005 g of pyriproxyfen are dissolved in ethanol to make the total 20 ml. Two milliliters (2.0 ml) of the solution were sprayed uniformly to a mouse having about 30 g of weight from 20 cm of the distance with a glass atomizer. The mouse was dried for one minute with drier, and then fastened by iron net. The fastened mouse was put in a glass container, and then 20 adult cat fleas, which had not sucked blood yet, were put therein. The number of dead fleas was examined after 24 hours from the treatment. After 3 repetitions of the test, the mortality of flea was 82.2%.

What is claimed is:

1. A pesticidal composition which comprises synergistic effective amounts of (E)-$N^1$-[(6-chloro-3-pyridyl)methyl]-$N^2$-cyano-$N^1$-methylacetamidine and pyriproxyfen as active ingredients and a carrier.

2. A pesticidal composition according to claim 1, wherein the weight ratio of (E)-$N^1$-[(6-chloro-3-pyridyl)methyl]-$N^2$-cyano-$N^1$-methylacetamidine and pyriproxyfen in the composition is in the range of from 1:0.01 to 1:10.

3. A method for controlling pests which comprises applying a synergistic effective amount of (E)-$N^1$-[(6-chloro-3-pyridyl)methyl]-$N^2$-cyano-$N^1$-methylacetamidine and pyriproxyfen to pest or place where pest inhabits.

4. A method for controlling pests according to claim 3, wherein the weight ratio of (E)-$N^1$-[(6-chloro-3-pyridyl)methyl]-$N^2$-cyano-$N^1$-methylacetamidine and pyriproxyfen in the composition is in the range of from 1:0.01 to 1:10.

5. A method for controlling pests harmful to crop which comprises applying a synergistic effective amount of (E)-$N^1$-[(6-chloro-3-pyridyl)methyl]-$N^2$-cyano-$N^1$-methylacetamidine and pyriproxyfen to plant or surrounding of plant.

6. A method for controlling pests according to claim 5, wherein the weight ratio of (E)-$N^1$-[(6-chloro-3-pyridyl)methyl]-$N^2$-cyano-$N^1$-methylacetamidine and pyriproxyfen in the composition is in the range of from 1:0.01 to 1:10.

7. A method for controlling ectoparasites of animal which comprises applying a synergistic effective amount of (E)-$N^1$-[(6-chloro-3-pyridyl)methyl]-$N^2$-cyano-$N^1$-methylacetamidine and pyriproxyfen to host animal.

8. A method for controlling pests according to claim 7, wherein the weight ratio of (E)-$N^1$-[(6-chloro-3-pyridyl)methyl]-$N^2$-cyano-$N^1$-methylacetamidine and pyriproxyfen in the composition is in the range of from 1:0.01 to 1:10.

* * * * *